United States Patent [19]

Francis et al.

[11] Patent Number: 5,858,789
[45] Date of Patent: Jan. 12, 1999

[54] METHOD FOR MAKING A RETICULOCYTE ASSAY CONTROL

[75] Inventors: Ralph T. Francis, Richfield; Alan M. Johnson, New Brighton, both of Minn.

[73] Assignee: Research & Diagnostic Systems, inc., Minneapolis, Minn.

[21] Appl. No.: 55,371

[22] Filed: Apr. 6, 1998

Related U.S. Application Data

[63] Continuation of Ser. No. 695,515, Aug. 12, 1996, Pat. No. 5,736,402, which is a continuation of Ser. No. 321,801, Oct. 12, 1994, abandoned.

[51] Int. Cl.⁶ .................................................. G01N 33/49
[52] U.S. Cl. ............................ 436/10; 436/63; 436/174; 436/175; 436/176; 436/177; 435/2; 435/29; 252/408.1
[58] Field of Search .................................. 436/8, 10, 63, 436/174, 175, 176, 177; 435/2, 29, 34, 39; 252/408.1

[56] References Cited

U.S. PATENT DOCUMENTS

| | | | |
|---|---|---|---|
| 4,324,686 | 4/1982 | Mundschenk | 436/10 |
| 4,338,564 | 7/1982 | Mundschenk | 324/71.4 |
| 4,447,547 | 5/1984 | Allen et al. | 436/543 |
| 4,704,364 | 11/1987 | Carver et al. | 436/10 |
| 4,777,139 | 10/1988 | Wong et al. | 436/18 |
| 5,320,964 | 6/1994 | Young et al. | 436/10 |
| 5,380,664 | 1/1995 | Carver et al. | 436/10 |
| 5,432,089 | 7/1995 | Ryan et al. | 436/10 |

OTHER PUBLICATIONS

Bulova et al., *The Journal of Biological Chemistry*, vol. 247, No. 10, pp. 3101–3106, May 25, 1972.
Tsuda et al. *American Journal of Clinical Pathology*, vol. 93, pp. 109–111, Jan. 1990.
Beutler, E. et al. *Journal Lab. Clin. Med.*, vol. 86(2), 1976.
Beutler, E. et al. *Blood Cells*, vol. 12, pp. 57–64, 1986.
Burton, A.R. "Automation of the Reticulocyte Count" Jan. 1994.
Davis, B. H. et al. *Annals New York Academy of Sciences* date unknown.
Houwen, B. "Reticulocyte Maturation", *Blood Cells*, vol. 18, pp. 167–186, 1992.
Koepke, J. F. et al. "Reticulocytes", *Clin. Lab. Haemat;* vol. 8, pp. 169–179, 1986.
Savage, R.A. et al. *Blood Cells*, vol. 11, pp. 97–112, 1985.
Tsuda, I. et al. *A.J.C.P.* Jan. 1990.
"Reticulocyte Counting by Flow Cytometry: Pro–posed Guideline" NCCLS document H44–P, vol. 13, No. 18, Nov. 1993.
"Body Fluids, Hematology & Immunology", *The Biology of the Pig*, pp. 254–255, 86–87, date unknown.
Retic–Chex from Streck Laboratories, Inc. Apr. 1993.
Retic–C from Coulter 1993.
TEST point™ Reticulocyte Control from Miles Laboratories date unknown.

*Primary Examiner*—Maureen M. Wallenhorst
*Attorney, Agent, or Firm*—Fredrikson & Byron, P.A.

[57] ABSTRACT

A pre-determined concentration of stabilized, maturation-arrested porcine reticulocytes in a red blood cell base, useful as a reticulocyte control composition. The composition can be provided in the form of a concentrated reticulocyte composition, to be diluted to a desired final reticulocyte concentration at the time of use. The composition can also be provided in the form of a diluted, ready-to-use control composition. Also included is a method of preparing such a composition, the method involving sequential steps of forming and sedimenting Rouleaux bodies.

2 Claims, No Drawings

METHOD FOR MAKING A RETICULOCYTE ASSAY CONTROL

This application is a continuation of application Ser. No. 08/695,515, filed Aug. 12, 1996, now U.S. Pat. No. 5,736, 402 issued on Apr. 7, 1998, which is a continuation of application Ser. No. 08/321,801, filed Oct. 12, 1994, now abandoned.

TECHNICAL FIELD

The present invention relates to the field of hematology, and in particular, to assays for determining the number or presence of reticulocytes in blood. In another aspect, the invention relates to control compositions for use in performing such assays, and to processes for preparing and methods of using such control compositions.

BACKGROUND OF THE INVENTION

The field of hematology involves the study of blood, including the discrete cell type populations that make up the blood. One important tool in this field involves the ability to reliably and accurately distinguish and count the various cell type populations. Clinical significance can be attributed to abnormal levels, in both relative and absolute terms, of most, if not all cell type populations.

In particular, the study of the kinetics of blood cell production and destruction depends on an assessment of the number of new cells being delivered to the circulation per unit time. New red cells (known as reticulocytes) are easily identified and can be quantified as a percentage of total red blood cells ("RBC's"). This percentage can be multiplied by the red cell count in order to provide the number per microliter.

In order to identify reticulocytes, the cells can be distinguished from mature red blood cells by the presence in reticulocytes of a distinctive stainable marker formed of mitochondria, ribosomes, and other cytoplasmic organelles. This marker is visible when precipitated by so-called supravital dyes, such as new methylene blue, brilliant cresyl blue, and acridine orange.

Reticulocytes require on the order of 3 to 4 days for maturation into mature (non-stainable) red blood cells, with about 2 to 3 days of this period being spent in the marrow itself, and about one day in the peripheral blood. Since approximately 1% of the circulating red cells in normal humans are replaced daily, and a newly released erythrocyte is identifiable as a reticulocyte for only about one day, it follows that under normal circumstances about 1% of circulating red cells are detectable as reticulocytes.

Variations in the reticulocyte count can be clinically significant, if detected with assurance. Levels approaching 3% (based on the total number of circulating red cells) are seen in instances of increased marrow activity, e.g., when blood synthesis is stimulated as by erythropoietin. In contrast, levels below about 0.5% can be an indication of bone marrow incompetence. Hence, a reticulocyte count is an effective measure of marrow erythroid output, since the release of one reticulocyte signals the production of one red cell by the marrow.

A wide variety of approaches have been described for determining absolute and/or relative reticulocyte levels. Although such approaches have traditionally been performed manually, automated procedures are being used with increasing frequency. An increasing number of major instrument manufacturers of automated cell counting instruments have added the ability to count reticulocytes to their systems in recent years. Some instruments provide values for what is known as a "reticulocyte maturation index", or "RMI". Although this parameter is not yet standardized for clinical reporting, it nevertheless shows great promise as a clinically useful parameter.

A common principle underlying the use of each method is the need for a reliable, standardized reticulocyte control composition, against which to assess the reliability of the results. Presently, reticulocyte controls are provided in a number of different forms. Human blood itself is generally considered to be unsuitable for the preparation of reticulocyte controls. Reasons for this include the safety concerns associated in recent years with the use of human blood products, as well as the fact that human blood is typically too low in reticulocyte count to be useful for the preparation of a wide range of control levels.

A control composition known as "Retic-C"™ is available in control levels I, II and III from Coulter Corporation (Miami, Fla.). This product includes avian red blood cells as the retigulocyte analogues. Such cells are not derived from true reticulocytes, however, nor do they stain in the manner common to reticulocytes. As a result, the composition is limited in use to automated instruments that rely on detection techniques other than traditional staining, such as the Coulter "STK-S"™ instrument. The avian cells are significantly larger than human reticulocytes and, in contrast to reticulocytes, also contain a nucleus.

Another control composition is a reticulocyte analogue product available as the "Retic-CHEX"™ product in concentrations of 1, 3, and 5% from Streck Laboratories (Omaha, Neb.). This control also suffers from a number of drawbacks, however, including poor staining intensity, and performance that is only minimally like that of true reticulocytes. Yet other control compositions, both of which are manufactured by Streck, include "Test Point"™ product (available in 2 and 5% levels for use with Miles/Technicon instruments), and a 2 and 5% level control available for instruments available from Sysmex. Both compositions are limited in that they provide only two levels, with the upper level being significantly lower than may be desired.

As a result, there do not appear to be any control compositions available on the market that provide an optimal combination of stability, true reticulocyte appearance and stain characteristics, and wide utility with most, if not all, presently available assay techniques. A reticulocyte control product capable of providing such attributes would be highly desirable.

SUMMARY OF THE INVENTION

The present invention provides a reticulocyte control composition comprising a predetermined concentration of stabilized, maturation-arrested porcine reticulocytes in a red blood cell base. In one preferred embodiment, the composition is in the form of a concentrated reticulocyte composition, having on the order of about 85% or more porcine reticulocytes (based on the total red blood cell count). The concentrate can be combined with a diluent porcine or human red blood cell base, e.g., having a similar total cell count, but on the order of 1% reticulocytes. The concentrate and diluent can be combined at the time of use, in order to achieve a desired final reticulocyte concentration.

In an alternative preferred embodiment, the concentrate composition can be included in a concentrate/diluent kit, together with one or more diluent RBC base compositions, for mixing at the time of use. In yet another preferred embodiment, a plurality of compositions are provided in dilute, ready-to-use kit form, the kit having a plurality of pre-determined concentrations of reticulocytes. Control compositions of the present invention provide an optimal combination of flexibility, concentration range, uniformity and shelf-life.

In another aspect, the invention provides a method of preparing a reticulocyte control composition, the method including the steps of: (1) harvesting an enriched population of porcine reticulocytes; (2) arresting further maturation of the reticulocytes and stabilizing the harvested, arrested reticulocytes; and (3) preparing a control composition comprising the stabilized, maturation-arrested reticulocytes.

A preferred method of the invention involves the initial step of preparing a fraction of porcine blood that is enriched for the presence of reticulocytes. In a particularly preferred embodiment, the method of the present invention is integrated with present-day preparative procedures involving other uses of porcine blood, e.g., the recovery of porcine platelets.

Applicants have found that existing procedures for the recovery of porcine platelets can also be used to provide fractions that are enriched in the presence of reticulocytes. Such fractions provide a useful and cost-effective starting point for the preparation of reticulocyte control compositions. The resulting control compositions provide an optimal combination of stability, true reticulocyte appearance and stain characteristics, and wide utility as a control with most, if not all, presently available assay techniques.

DETAILED DESCRIPTION

Applicants have observed that porcine blood provides a naturally higher level of reticulocytes, as compared to humans, and discovered that these reticulocytes can be recovered and stabilized in a manner that renders them useful as a reticulocyte control composition. Porcine reticulocytes appear to enter the circulation earlier, and in turn tend to be younger in appearance than counterpart cells in human blood. As such, they provide an opportunity to recover a substantially homogeneous population of cells that can then be arrested to minimize further development, and provided in arrested, stabilized form.

A preferred method involves sequential sedimentation steps, both of which involve the formation and sedimentation of "Rouleaux bodies", as described below. In the first step, a platelet-rich supernatant and corresponding reticulocyte-rich sediment fraction are formed. The platelet rich supernatant can be removed and used for other purposes, while the sediment fraction can be resuspended and subjected to a second sedimentation step. The supernatant fraction formed as the result of the second sedimentation step has been found to be particularly rich in reticulocytes. The second sediment fraction, in turn, has been found to be particularly useful as a diluent base.

In a preferred embodiment, the reticulocyte-rich second supernatant fraction contains on the order of 80% to 95% or more reticulocytes (as a percentage of the total RBC's per unit volume). Correspondingly, the second sediment fraction contains on the order of 0.5% to 1% reticulocytes. Accordingly, desirable control compositions having any level between 0.5% and 95% or more can be prepared by judicious combination of the second supernatant and sediment (diluent) fractions.

Applicants have found that dextran-induced Rouleaux formation can be used to provide an efficient separation of reticulocytes and mature red blood cells for the purpose of the present invention. The ability to control the manner and extent to which Rouleaux bodies will sediment with and without reticulocytes serves as the basis for the unique two-step sedimentation protocol of this preferred method.

Reticulocytes are immature red blood cells. In both human and porcine blood, the reticulocytes tend to be larger and less concave than their corresponding mature red blood cells. Reticulocytes also tend to possess higher surface charge densities than the corresponding fully mature cells. As a result, at least in porcine blood, reticulocytes do not generally form Rouleaux bodies, either with each other or with mature red blood cells. Under suitable circumstances, however, Applicants have found that porcine reticulocytes can nevertheless be caused to sediment with Rouleaux bodies.

In contrast, Applicants have discovered that under certain conditions human reticulocytes can form Rouleaux bodies in the presence of mature human red blood cells. As a result, the method described in the present invention finds greater utility with porcine reticulocytes, which are much easier to separate from the mature porcine red cell population.

Additionally, pigs normally possess approximately twice as many reticulocytes (as a percentage of total red blood cells per unit volume) in comparison to humans. Applicants have found that the relative abundance of reticulocytes, the large volumes of blood that are available, and the strong discrimination against reticulocyte Rouleaux formation in the pig, can all be used to effectively produce large volumes of an enriched fraction having a high reticulocyte concentration.

As used in this application the term "reticulocyte control" will refer to a suspension of porcine cells useful as a control in one or more manual or instrument-based assays for determining the number or level of natural, e.g., human, reticulocyte cells. The word "arrest", and inflections thereof, will refer to porcine reticulocytes that are substantially inhibited, either reversibly or irreversibly, from undergoing further natural maturation in a manner that would diminish their utility as a reticulocyte control. Typically, maturation of reticulocytes corresponds with a loss of distinctive cellular material that is stainable with conventional chromogenic or fluorogenic paravital dyes.

The word "stabilize", and inflections thereof, as used herein, will refer to arrested cells that are provided in a form that allows the cells to be stored and used in a manner that does not unduly diminish their utility as a reticulocyte control. Generally, stabilization involves the preparation of a suspension containing such cells in combination with one or more ingredients that are useful as preservatives. In a preferred embodiment, reticulocyte control compositions are provided in the form of concentrated suspensions having 2 month, and preferably 3 month or longer shelf stability when stored under refrigeration.

Compositions of the present invention can be prepared from whole porcine blood, or fractions thereof, according to any suitable preparative procedure. The following is a general description of a preferred method for the harvest of porcine reticulocytes and preparation of a reticulocyte control composition having a plurality, e.g., three, concentration levels.

Porcine blood can be recovered from any suitable source. Preferred procedures for the preparation of platelets involve the recovery of porcine blood from freshly slaughtered pigs. One particular advantage of the preferred method of the present invention is that blood can be used for the recovery of reticulocytes in a manner that is compatible with the use of the blood for other purposes, e.g., the recovery of platelets.

U.S. Pat. Nos. 4,324,686 and 4,338,564, the disclosures of which are incorporated herein by reference, describe methods for the preparation of compositions and controls containing porcine blood platelets. The methods described in these patents are particularly preferred for use in the initial steps of the presently claimed method.

In one embodiment of the method of the invention, a first sedimentation step is employed in order to provide a platelet-rich supernatant, and a reticulocyte-rich sediment fraction. The method involves the use of a reagent such as a citrate-citric acid-dextran ("CCD") reagent, which is added to whole blood to facilitate the separation of a red blood cell sediment or pellet, and a platelet-rich plasma supernatant.

Newly recovered blood is added directly to a fill large (e.g., 20 liter) carboy containing a suitable amount of the dextran-based anticoagulant concentrate. A suitable formulation for the preparation of an anticoagulant/dextran concentrate is provided below. Given the teaching of the present invention, those skilled in the art will be able to determine the actual amount of the anticoagulant/dextran concentrate that is sufficient to prevent blood clot formation in the blood sample, while at the same time allow Rouleaux formation of red blood cells as described below. The dextran has been a useful component in the collection of porcine blood for the purpose of harvesting platelets from the fresh porcine blood.

The Rouleaux effect can be assessed by microscopic evaluation of a sample of blood. The effect is typified by a distinctive stacking or aggregating of mature red blood cells together in rows. Mature red blood cells, both porcine and human, are bi-concave in shape and have a relatively low surface chemical charge. These properties allow them to form the Rouleaux bodies in the presence of a high molecular weight polysaccharides (e.g., dextran) or polypeptides (e.g., gelatin).

The mixture of whole blood and CCD concentrate is prepared and allowed to settle at room temperature for one to three hours. After settling, a dense sediment is formed that is dark red in appearance. Above the sediment there is a translucent pink-colored, platelet-rich supernatant. The supernatant (generally representing about 12 liters of the original 20 liters) is removed, as by aspiration or gentle pouring, taking care not to disturb the interface.

Applicants have discovered that the sediment is particularly rich in reticulocytes, even though reticulocytes are not believed to themselves form Rouleaux bodies with mature RBC's. Rather, it appears that the reticulocytes are trapped within or between, but do not actually form a part of, the Rouleaux bodies formed by the pig RBC's. In order to recover the reticulocytes, this first sediment is resuspended to the original sample volume by the addition of diluted CCD. The diluted CCD is added to achieve or maintain a final concentration of CCD equivalent to the concentration achieved in the first mixture of blood and CCD concentrate.

The resuspended first sediment is incubated overnight (e.g., about 15 hours) at room temperature, in order to again allow the formation and settling of Rouleaux bodies. Upon incubation there again appears a lower compact cell sediment, and an upper supernatant fraction that is darker red in appearance than the first supernatant. The two fractions are separated, washed, and assayed in order to obtain concentrated and diluent reticulocyte phases.

The supernatant of the second sedimentation has been found to be particularly rich in reticulocytes. Upon removal from the second sediment, the supernatant is preferably filtered by any suitable means, in order to remove white blood cells and platelet aggregates. In the preferred filter method described below, the supernatant is filtered through a cellulose slurry filter. White blood cells ("WBC") and platelets are retained by the slurry, while the filtrate is collected and assayed to ensure that the WBC and platelet levels are within desired specifications. Typical specifications include 2,000 or less WBC's, and 40,000 or less platelets, per microliter.

The filtered reticulocyte-containing suspension is then centrifuged to concentrate the cells, which are then resuspended in a liquid medium designed to stabilize the cells and substantially arrest further reticulocyte maturation.

The second sediment fraction is also recovered, then washed one or more times to remove WBC's and platelets, and finally resuspended to a desired extent to serve as a low-reticulocyte diluent.

Preferably in the course of the above process the enriched porcine reticulocytes are arrested from further maturation and stabilized. The inhibition of maturation and the stabilization of the cells can be accomplished by resuspending the cells in a suitable medium. Applicants have discovered that media such as those described previously for the recovery of pig platelets can be useful for preparing a reticulocyte composition as well. As a result, the method and composition of the present invention can be integrated with platelet recovery methodologies in order provide an optimal and cost effective use of the blood.

A medium useful for the recovery and storage of porcine reticulocytes, which will be referred to for brevity as a "Retic Medium", is provided in the form of a buffered solution maintained at a pH between pH 7 and pH 8. The solution preferably includes a protein synthesis inhibitor or other metabolic inhibitor capable of arresting mammalian red cell development. Preferred inhibitors include natural antibiotics such as cycloheximide, and semisynthetic antibiotics such as rifampin, each used at a final concentration of about 0.25 to 1% (by weight, based on the volume of the medium).

The Retic Medium also preferably lacks a carbon or other energy source useful for continued metabolism. In the absence of maturation inhibitors and/or in the presence of an energy source, reticulocytes may continue to develop and lose their stainable RNA material, even at lower temperatures.

Cycloheximide is particularly preferred, since it appears to provide an irreversible stabilizing effect on the porcine reticulocytes. Attempts to induce maturation in porcine reticulocytes after brief exposure to Retic Medium containing cycloheximide have resulted in reticulocytes that do not lose their stainable RNA/protein material. Thus, with regard to the detectable marker for reticulocyte enumeration (cytosolic ribonucleoprotein), the porcine reticulocytes appear to be stabilized.

More preferably, the solution includes one or more preservatives, in order to provide the final composition with prolonged shelf life stability. For example, fairly young reticulocytes in human blood cell samples were found to be stable after storage for over 2 months at 4° C. in a Retic Medium such as exemplified below. Suitable preservatives include, but are not limited to, nalidixic acid (an antibacterial agent); p-hydroxybenzoate methyl ester and p-hydroxybenzoate propyl ester (antibacterial agents); and penicillin (antibacterial).

A control composition of the present invention can be used according to established laboratory hematology procedures, for instance, as a control to calibrate or monitor the performance of diagnostic tests. Preferred compositions are composed of stable materials that provide a means of verifying accuracy and precision of reticulocyte counting methods, and can be handled in the same manner as patient specimens.

A composition of the present invention is preferably provided in the form of an in vitro diagnostic reagent that includes arrested, stabilized porcine reticulocytes in combination with porcine, human, or other mammalian erythrocytes, all suspended in a plasma-like fluid containing suitable preservatives. Any human blood components used in the preparation of such a composition should be suitably tested in order to ensure that it is negative for all necessary infectious agents or indicators, including hepatitis B surface antigen (HBsAg), hepatitis C virus antibody (anti-HCV), and human immunodeficiency virus antibody (anti-HIV). Since no test available can provide total assurance that specimens of human origin will not transmit infectious disease, particular care should be used with any such composition.

In a preferred embodiment, a composition of the present invention is used to prepare a plurality of control levels, e.g., three levels representing normal, moderately high, and very high levels of reticulocytes.

A control composition of the present invention is typically provided in the form of a kit containing a plurality of different reticulocyte concentrations. A typical kit includes separate vials containing reticulocytes at a plurality of concentrations ranging between about 0.5% to about 25%. Most preferably, the concentrations range between about 1% and 15%, and even more preferably, between about 1% and 12%. A preferred kit, for instance, includes a plurality of concentrations, e.g., 1%, 5%, and 12%.

Concentrations over about 25% tend to have little clinical usefulness, since they are rarely encountered in practice. On the other hand, concentrations less than about 0.5%, are difficult to determine with both accuracy and precision by conventional detection techniques.

Compositions of the present invention are particularly stable in storage, and are preferably stored upright at temperatures of between 2° and 8° C. when not in use. Compositions should be protected from overheating and freezing. Unopened vials containing such compositions are stable until the expiration date, while opened vials are stable for at least 14 days provided they are handled properly. A prepared sample of a composition of this invention is stable for on the order of 60 to 90 minutes.

Diluted, ready-to-use compositions of the invention are generally similar in appearance to fresh whole blood. It is normal for a light pink-tinted supernatant to form upon settling. Discoloration of the supernatant fluid or visible hemolysis may indicate product deterioration. Overheating, freezing, rough handling, and contamination are frequent causes of product damage. Inability to recover expected values may also indicate product deterioration. Incomplete mixing, instrument malfunction, or defective stains are other causes of unacceptable results. A composition should not be used if deterioration is suspected.

In use, a vial containing the composition of the present invention is typically removed from refrigerated storage and allowed to warm to room temperature. The composition is then mixed by gently rolling the vial between the palms of the hands, and inverting the vial until the cells appear to be completely and uniformly suspended. Care should be taken to avoid undue agitation of the vial, such as by use of a vortex, since agitation can disrupt the cells.

The composition can then be incorporated into the analytical procedure of choice in the same manner as a patient sample, for instance with automated methods, the control is analyzed in the manner provided with the operator's manual for the particular instrument.

The composition should be used within a reasonable time, depending on the particular method employed (e.g., within about 60 minutes, after warming to room temperature). After removing an aliquot from the vial, the control composition can be re-stored for later use by carefully wiping the vial rim and cap and returning the capped vial to the refrigerator.

Assay values are typically presented as a mean and a range. The mean is derived from replicate testing by the specific method. Instruments used for automated methods are operated and maintained according to the instrument manufacturer's instructions. The manual method is a direct microscopic count using the conventional reticulocyte counting procedure with new methylene blue stain.

The range is an estimate of variation between laboratories and takes into account inherent imprecision of the method, differences in maintenance, operating technique, and equipment. It is recommended that each laboratory establish its own laboratory-specific ranges for greater control sensitivity.

Assay values on a new lot of control should be confirmed before it is put into routine use. The laboratory recovered mean should be within the assay range. Laboratories may consider results acceptable when at least 95 percent of results are within 2 Standard Deviations of the laboratory mean.

A composition of the present invention can be used as a control composition in most, if not all, of the following conventional methods for reticulocyte evaluation.

Manual (microscopic):

A suitable procedure for the manual evaluation of reticulocytes involves the mixing of an equal amount of blood with a supravital stain, e.g., new methylene blue or brilliant cresyl blue, and incubating the mixture for approximately fifteen minutes. This incubation period allows the RNA to precipitate with protein as a complex, which then appears as a dark blue network that allows reticulocytes to be identified and enumerated microscopically.

The sample is mixed well and three wedge smears are prepared. In one approach, a technician can examine the smear and count 500 cells under the 100× oil objective. Using a standard "bafflement" pattern, the red blood cells and reticulocytes are counted simultaneously using separate cell counters. A second technician can use the same technique on a different smear. The two counts must agree within 10%. If they do not, a third smear should be counted. The reticulocyte percent is calculated as follows:

$$\% \text{ Reticulocytes} = \frac{\text{number of reticulocytes in 1000 red blood cells}}{10}$$

Another approach involves the use of a Miller disc inserted into an eyepiece. The disc is composed of two squares. The area of the smaller square is ⅑ that of the larger square. The red blood cells are counted in the smaller square, while the reticulocytes are counted in the larger square. Cells should be counted in 20 successive fields. Using this approach, the reticulocyte percent can be calculated as follows:

$$\% \text{ Reticulocytes} = \frac{\text{total reticulocytes in large squares}}{\text{total red bloods cells in small squares} \times 9}$$

Caution must be taken to ensure that cellular inclusions, such as Howell-Jolly bodies and Heinz bodies, are not confused with the identification of reticulocytes. Precipitated stain and refractile artifact must also be distinguished from reticulocytes.

Control compositions of the present invention perform particularly well in manual assays. The porcine reticulocytes are quite similar in both appearance and performance to human reticulocytes. They also tend to be young and easily identifiable. Even at higher concentrations, the porcine reticulocytes provide a useful visual contrast between the reticulocytes and unstained, mature RBC's.

Flow Cytometry:

Thiazole orange has proven to be the reticulocyte fluoroindicator of choice when counting reticulocytes on a semi-automated flow cytometer such as a Becton Dickinson FACScan, Coulter EPICS or an Ortho Spectrum™. Staining with thiazole orange increases with time and temperature, and those skilled in the art will appreciate the manner in which these parameters can be standardized. Thiazole orange is available from Becton Dickinson in pre-diluted form as the product known as "ReticCOUNT"™.

Yet another fluorescent indicator, known as "auramine o" is currently used on reticulocyte automated flow cytometers available from Sysmex, but has not found favor in the semi-automated cytometers. A recently developed fluorochrome that may find use for flow cytometric reticulocyte counting is known as "Syto 12"™ from Molecular Probes of Eugene, Oreg. This dye is one of several new supravital stains that permeate cells rapidly and produce high fluorescent yields upon binding to nucleic acids.

SYSMEX R-1000 AND R-3000™:

In 1989, TOA Medical Electronics Co. LfD, Hobe Japan, introduced a benchtop flow cytometer known as the "Sysmex R-1000"™ automated reticulocyte analyzer. Three years later, an upgraded R-series analyzer, the R3000™ was released. The blood sample is aspirated, diluted and stained automatically by both instruments. The supravital dye used is auramine o, which carries a positive charge, resulting in an attraction to the negatively charged ribonucleic acid (RNA) and deoxyribonucleic acid (DNA). The samples are hydrodynamically focused and passed through a flow cell. The cell is illuminated by an argon laser beam at a wavelength of 488 nm.

The R-3000™ measures forward fluorescence using a filter to obstruct a shorter wavelength of light and a photo-multiplier tube to determine the intensity. The R-1000™ measures side fluorescence using a filter placed at a 90 degree angle to the laser beam path. The forward scatter measures the cell size and fluorescence indicates the RNA content of the sample. The fluorescence and scattered light of the individual cells allow these instruments to count the reticulocytes. The instruments analyze about 30,000 cells per sample, determining the reticulocyte count, reticulocyte ratio, and total RBC count. This methodology can analyze far more cells than the manual method, thus increasing the reproducibility and precision. Both instruments use scattergrams divided into three areas to display results. These areas are platelets, mature RBC's and reticulocytes.

The reticulocyte area is further divided into three areas; low fluorescence ratio (LFR), middle fluorescence ratio (MFR) and high fluorescence ratio (HFR). An additional area that displays very high fluorescent events counts "shift" cells, nucleated RBCs and cells containing Howell-Jolly bodies. These cells are not included in the reticulocyte count. The area is found above the upper limit of most reticulocytes and below the WBC region.

MILES DIAGNOSTICS H*3™:

Miles Diagnostics/Technicon introduced the H*3™ hematology analyzer during 1993, partly in response to the growing demand for automated reticulocyte counting. The H*3™ is a semi-automated flow cytometer that analyzes RBC's using the same technology as previously used in the H*1 and H*2™ analyzers, but also measuring hemoglobin content as well. The value of measuring the hemoglobin content of reticulocytes has been described in support of this unique feature of the H*3.

Coulter STKS/MAXM:

The Coulter Corporation has developed an upgrade for their STXS and MAXM™ hematology analyzers. Using their VCS technology (Volume, Conductivity and Scatter), the upgrade provides reticulocyte percentage values base on new methylene blue staining characteristics of the reticulocytes. The procedure requires two offline steps. First, samples are diluted into a new methylene blue solution and incubated at room temperature for between 5 and 60 minutes. Second, a small volume of the stained sample is diluted with a clearing solution that clears the cellular hemoglobin but preserves the RNA-new methylene blue complex. In addition to the reticulocyte percentage and absolute number, the mean reticulocyte volume and reticulocyte maturation index parameters are available as well.

Control compositions of the present invention also perform quite well in each of the automated systems described above, using methodologies suggested by the manufacturers and within the skill of those in the art.

The invention will be further described with reference to the following non-limiting examples.

EXAMPLES

Reagent Preparation

The following reagents were prepared in advance:

CC Dextran (stock solution)

The following ingredients were combined and made to 60 liters with deionized water: NaOH (24 g), citric acid (142.63 g), sodium citrate (3210 g), (3600 g) Dextran (Sigma No. D-4876, molecular weight range 150 kd to 180 kd).

CC Dextran (diluted)

The "CC Dextran" solution was diluted 1:7.1 with standard phosphate buffered saline (pH 7.5±0.1) having (0.1%) azide as a preservative ("PBSN") (i.e. for 12 liters final, 1.69 liters of CC Dextran plus 10.31 liters of PBSN).

Cellulose Slurry

The following ingredients were added to a 2 liter flask (each cellulose product was obtained from Sigma Chemical Co.):

100 g Cellulose, alpha cellulose fiber 50 g Cellulose, microgranular 50 g Cellulose (Sigmacell Type 50)

Retic Medium (to 1.5 liters)

The ingredients were thoroughly mixed and care was taken to ensure that the cellulose slurry was thoroughly resuspended and mixed just prior to pouring into funnel beds.

| Retic Medium Component | Units | Qty/L |
| --- | --- | --- |
| Albumin, Bovine | mL | 100.0 |
| Chloride, Potassium | g | 4.0 |
| Citrate, Tripotassium | g | 3.0 |
| Cycloheximide | g | 0.5 |
| Phosphate, Dipotassium | g | 5.0 |

The ingredients were combined and the solution made to a pH of 7.5 (±0.1), with an osmolality of approximately 340 (±15). After the ingredients were added to the solution, sterile filtration was accomplished by peristaltic pumping through a terminal 0.2 micron minicapsule filter of 500 square cm surface area.

Example 1

Porcine reticulocytes were harvested and prepared as a control composition in the following manner:

1. Recovery of porcine blood.

At a slaughter house, porcine blood was recovered from freshly slaughtered pigs and added to fill 20 liter carboys containing 2.5 liters of "CCD" concentrate (prepared as described above). The final concentration of the CCD concentrate upon filling the carboy with fresh porcine blood was determined such that blood clotting would be prevented and the red blood cells would exhibit the desired Rouleaux effect.

2. First Rouleaux sedimentation.

The blood/CCD mixture was gently transported by truck to the laboratory and allowed to continue to settle, for a total incubation time of approximately 3 hours. Upon settling, a dense sediment was formed that was dark red in appearance. Above the sediment there was a sharp interface between the sediment and the translucent pink-colored, platelet-rich supernatant.

3. Separation of first sediment and supernatant.

The supernatant (approximately 12 liters of the original 20 liters) was removed by aspiration, taking care not to disturb the interface. The interface (approx. 0.5 liters) was then gently removed as well, by aspiration, and discarded. The Rouleaux effect in the first sediment fraction was confirmed by microscopic examination which revealed distinctive mature red blood cells stacking or aggregating together in rows.

4. Dilution of first sediment second sedimentation.

In order to recover entrapped reticulocytes, the first sediment was resuspended to the original sample volume (20 liters) by the addition of approximately 12 liters of diluted CCD, prepared as described above. The resuspended first sediment was incubated overnight (e.g., about 15 hours) at room temperature, in order to allow the formation and second settling of Rouleaux bodies. Upon incubation there again appeared a lower compact cell sediment, and an upper supernatant fraction that was darker red in appearance than the first supernatant.

5. Separation of second sediment and supernatant.

The upper phase was slowly aspirated to form one liter fractions, down to a level approximately 2 cm above the resedimented RBC phase. The two fractions were separated, washed, and assayed as described below in order to obtain concentrated and diluent reticulocyte phases.

6. Processing of second sediment.

The second sediment fraction was recovered, washed to remove WBC's and platelets, and finally resuspended to serve as a low-reticulocyte diluent. The sediment was resuspended to a concentration of 3.8 to 4.2 million cells per microliter, as determined by analysis on a Coulter S-4 instrument. Within this suspension, it was found that between about 0.5% and 1% were identifiable as reticulocytes.

Approximately one-half of the recovered second supernatant was available for recovery. Optionally, where the reticulocytes are to be diluted in a porcine RBC base composition, the remaining 2 cm interface between the upper phase and sedimented phase can be aspirated and stored separately.

7. Processing of second supernatant.

Upon removal from the second sedimentation step, the supernatant was diluted with Retic Medium to achieve a total cell count of between 0.4 and 0.6 million cells per microliter. The diluted supernatant was then filtered in order to remove white blood cells and platelet aggregates. The supernatant was filtered through a cellulose slurry filter using the slurry composition described above. WBC's and platelets were retained by the slurry, while the filtrate was collected and assayed to ensure that the WBC and platelet levels were within specifications.

All final filtrates (reticulocyte preparations with WBC and platelet levels within specifications) were centrifuged at 4500 RPM in a GSA rotor (RC5 Sorvall centrifuge) for 15 minutes in order to concentrate the reticulocytes.

The supernatant was poured off and the pellet resuspended in Retic Medium. The platelet level in the resuspended pellet was determined and if above specified limits, the sample was further diluted with Retic Medium and re-centrifuged in the GSA rotor at 2,000 RPM for 3 minutes. The next supernatant was gently poured off to provide a soft pellet. This process was repeated until the platelet amount was within specifications.

The final pellet was resuspended in Retic Medium to achieve a concentration of 3.8 to 4.2 million cells per microliter, as determined by analysis on a Coulter S-4 instrument. It has been found that, depending on the particular preparation, between about 80% and about 95% of the cells in this final suspension are identifiable as reticulocytes.

8. Preparation of control levels.

The final assayed fractions were used to prepare various control levels (1%, 5%, and 12%) for use in a control kit. In order to provide control compositions having porcine reticuloyctes in a porcine RBC base, suitable mixtures were made of the (1%) suspension formed in step 6 above, with the (80–95%) suspension formed in step 7.

In order to provide control compositions having porcine reticulocytes in a human RBC base, suitable mixtures were made of the suspension formed in step 7 above with a human cell isolate prepared as described below.

Human red cells that had been isolated from blood plasma were purchased from a commercial vendor of diagnostic blood. The packed cells were received in one-unit blood bags, and were pooled upon receipt. The pooled blood was then further processed in repetitive steps in order to remove non-RBC components.

The pooled samples were centrifuged for 20 minutes at 2500 RPM. White cell material was removed from the top of the resultant soft cell pellet. The pellet was repeatedly washed until the white blood cell and platelet concentrations in the pellet were within desired specifications. The final washed cell pellet was then resuspended to a concentration of 3.8 to 4.2 million cells per microliter and used as the lower diluent and a human RBC base.

Example 2

Concentrated and dilute reticulocyte compositions prepared as described in Example 1 were combined at various proportions and used in triplicate to determine the correlation between a standard flow cytometric technique (EPICS)™ and various manual and automated reticulocyte determination techniques. The results can be seen in TABLES 1 and 2 below. The data shows that the correlation between the EPICS™ technique and the various other techniques is consistently very close. When properly constructed, the data derived with the present reticulocyte compositions can provide accurate and useful values for RMI as well. The data indicates that the reticulocyte preparations of the present invention have wide applicability in most, if not all, presently available instruments and techniques.

TABLE 1

Correlation Data

| Technicon H*3 vs. EPICS ™ Profile II | | Coulter STKS vs. EPICS ™ Profile II | | Sysmex R1000 vs. EPICS ™ Profile II | |
|---|---|---|---|---|---|
| H*3 | EPICS | STKS | EPICS | R1000 | EPICS |
| 0.7 | 0.6 | 0.8 | 0.8 | 0.4 | 0.8 |
| 0.7 | 0.7 | 1.3 | 1.0 | 0.4 | 0.8 |
| 4.5 | 4.3 | 3.6 | 3.6 | 0.6 | 0.5 |
| 4.6 | 4.5 | 3.6 | 3.3 | 0.7 | 0.9 |
| 5.9 | 5.7 | 5.5 | 5.6 | 0.7 | 0.7 |
| 6.9 | 6.8 | 5.6 | 7.0 | 4.7 | 4.4 |
| 8.1 | 8.0 | 7.9 | 6.5 | 5.0 | 5.8 |
| 8.1 | 8.9 | 8.9 | 8.1 | 5.0 | 5.8 |
| 10.4 | 11.5 | 18.4 | 17.2 | 5.2 | 5.7 |
| 11.7 | 12.0 | 25.6 | 25.6 | 5.3 | 5.2 |
| 13.3 | 14.4 | 35.4 | 33.9 | 9.5 | 8.5 |
| 13.5 | 12.6 | | | 10.6 | 11.6 |
| 16.0 | 16.0 | | | 10.8 | 11.7 |
| 16.1 | 16.3 | | | 11.0 | 12.2 |
| 26.1 | 27.9 | | | 11.6 | 11.7 |
| 26.4 | 26.3 | | | | |
| 28.4 | 31.0 | | | | |
| 33.9 | 35.5 | | | | |
| 40.4 | 42.9 | | | | |
| 54.7 | 57.7 | | | | |
| 63.8 | 66.9 | | | | |

TABLE 2

Correlation Data

| NMB Manual vs EPICS ™ Profile II | | Sysmex R3000 vs. EPICS ™ Profile II | |
|---|---|---|---|
| NMB | EPICS | R3000 | EPICS |
| 0.4 | 0.8 | 0.5 | 0.7 |
| 0.6 | 0.7 | 0.6 | 0.7 |
| 0.6 | 0.8 | 0.7 | 0.8 |
| 0.8 | 0.8 | 4.8 | 5.4 |
| 6.0 | 6.4 | 4.9 | 5.4 |
| 6.2 | 6.8 | 5.0 | 5.4 |
| 6.8 | 7.4 | 5.2 | 5.5 |
| 7.8 | 7.0 | 5.4 | 5.5 |
| 8.0 | 7.6 | 5.4 | 5.4 |
| 8.2 | 7.3 | 9.7 | 10.7 |
| 12.0 | 12.9 | 10.0 | 10.9 |
| 12.6 | 12.9 | 10.2 | 10.9 |
| 13.8 | 13.5 | 10.3 | 11.0 |
| 14.2 | 14.7 | 10.6 | 11.0 |
| 15.6 | 16.1 | 10.8 | 11.1 |

We claim:

1. A method of preparing a reticulocyte control composition, the method including the steps of: (1) harvesting an enriched population of porcine reticulocytes; (2) arresting further maturation of the reticulocytes and stabilizing the harvested, arrested reticulocytes; and (3) preparing a control composition comprising a pre-determined concentration of stabilized, maturation-arrested reticulocytes by placing a predetermined concentration of the stabilized, maturation-arrested porcine reticulocytes in a red blood cell base, wherein the red blood cell base comprises detectable, mature erythrocytes.

2. A method according to claim 1 wherein the harvesting step involves sequential sedimentation steps of Rouleaux bodies in which reticulocytes tend to sediment in a first sedimentation step, and tend to not sediment in a second sedimentation step.

* * * * *